US010213452B2

(12) United States Patent
Aguilera Peralta et al.

(10) Patent No.: US 10,213,452 B2
(45) Date of Patent: Feb. 26, 2019

(54) PHARMACEUTICAL COMPOSITIONS CONTAINING STEVIOSIDES

(71) Applicant: FRESENIUS MEDICAL CARE DEUTSCHLAND GMBH, Bad Homburg (DE)

(72) Inventors: Abelardo Isaac Aguilera Peralta, Madrid (ES); Manuel Lopez-Cabrera, Madrid (ES); Rafael Selgas Gutierrez, Madrid (ES); Sonja Steppan, Neu-Isenburg (DE); Jutta Passlick-Deetjen, Seelbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 15/523,591

(22) PCT Filed: Oct. 28, 2015

(86) PCT No.: PCT/EP2015/074955
§ 371 (c)(1),
(2) Date: May 1, 2017

(87) PCT Pub. No.: WO2016/066672
PCT Pub. Date: May 6, 2016

(65) Prior Publication Data
US 2017/0304335 A1 Oct. 26, 2017

(30) Foreign Application Priority Data
Oct. 31, 2014 (EP) .................................... 14191301

(51) Int. Cl.
| A61K 31/704 | (2006.01) |
| C07H 15/24 | (2006.01) |
| C07C 62/34 | (2006.01) |
| A61K 47/26 | (2006.01) |
| A61M 1/16 | (2006.01) |
| C07C 62/32 | (2006.01) |
| A61M 1/28 | (2006.01) |
| A61K 9/08 | (2006.01) |

(52) U.S. Cl.
CPC .............. *A61K 31/704* (2013.01); *A61K 9/08* (2013.01); *A61K 47/26* (2013.01); *A61M 1/1654* (2013.01); *A61M 1/1668* (2014.02); *A61M 1/287* (2013.01); *C07C 62/32* (2013.01); *C07C 62/34* (2013.01); *C07H 15/24* (2013.01)

(58) Field of Classification Search
CPC ..... A61M 1/1654; A61M 1/287; A61K 31/19; A61K 31/191; A61K 31/704; C08C 62/32; C08C 62/34; C07H 15/24
See application file for complete search history.

(56) References Cited

U.S. PATENT DOCUMENTS

| 37,234,110 | | 3/1973 | Persinos |
| 4,082,858 | A | 4/1978 | Morita et al. |
| 4,339,433 | A | 7/1982 | Kartinos et al. |
| 4,649,050 | A | 3/1987 | Veech |
| 4,761,237 | A | 8/1988 | Alexander et al. |
| 2010/0179097 | A1* | 7/2010 | Tan ........................ A61K 31/19 514/23 |
| 2011/0091628 | A1* | 4/2011 | Abelyan .................. A23G 9/34 426/548 |
| 2013/0056678 | A1 | 3/2013 | Fenn et al. |

FOREIGN PATENT DOCUMENTS

| DE | 102010012183 | 9/2011 |
| JP | 03277275 | * 12/1991 |
| WO | WO 00/33851 | 6/2000 |

OTHER PUBLICATIONS

Caplus abstract of JP 03277275. (Year: 1991).*
Khaibullin, R. et al "O-alkylation of diterpenoid steviol . . . " Russ. J. Gen. Chem., vol. 79, No. 10, pp. 2197-2200. (Year: 2009).*
Hsu, Y. et al "Antihypertensive effect of stevioside . . . " Chin. Med. J. (Taipei), vol. 65, pp. 1-6. (Year: 2002).*
Priwat et al. A natural plant-derived dihydroisosteviol prevents cholera toxin-induced intestinal fluid secretion. The Journal of Pharmacology and Experimental Therapeutics, vol. 324, No. 2, pp. 798-805, Nov. 27, 2007.
Hashemi et al. The effect of rebadioside A on attenuation of oxidative stress in kidney of mice under acetaminophen toxicity, Iranian Journal of Toxicology Volume, vol. 7, No. 23, p. 944-951, Jan. 1, 2014.
Melis. Effect of Steviol on renal function and means arterial pressure in rats, Phytomedicine, Gustave Fischer Verlag, fol. 3, No. 3, pp. 349-352, Jan. 1, 1997.
Brahmachari et al. Stevioside and related compounds—molecules of pharmaceuticalpromise: a critical view, Archiv Der Pharmazia, vol. 344, No. 1, pp. 5-19, Jan. 25, 2011.
Rippe et al. Computer simulations of ultrafiltration profiles for an icodextrin based peritoneal fluid in CAPD, Kidney International, vol. 57, issue 6, pp. 2546-2556 (Jun. 2000).
Gotloib. The mesothelium under the siege of dialysis solutions: old glucose, new glucose, and glucose-free osmotic agents, Advances in Peritoneal Dialysis, vol. 25, 2009.
Schilte et al. Factors contributing to peritoneal tissue remodeling in peritoneal dialysis, Peritoneal Dialysis International, vol. 29, pp. 605-617. Feb. 2009.
Yong-Lim Kim, Update on Mechanisms or Ultrafiltration Failure, Peritoneal Dialysis International, vol. 29, supplement 2, abstract.

* cited by examiner

*Primary Examiner* — Leigh C Maier
(74) *Attorney, Agent, or Firm* — Jacobson Holman, PLLC.

(57) ABSTRACT

The present invention relates to pharmaceutical compositions containing steviol glycoside and or steviol glycoside derivatives as well as to their use as osmotics in particular for use in the treatment of chronic renal failure by dialysis.

13 Claims, 8 Drawing Sheets

PHARMACEUTICAL COMPOSITIONS CONTAINING STEVIOSIDES

Figure 1:
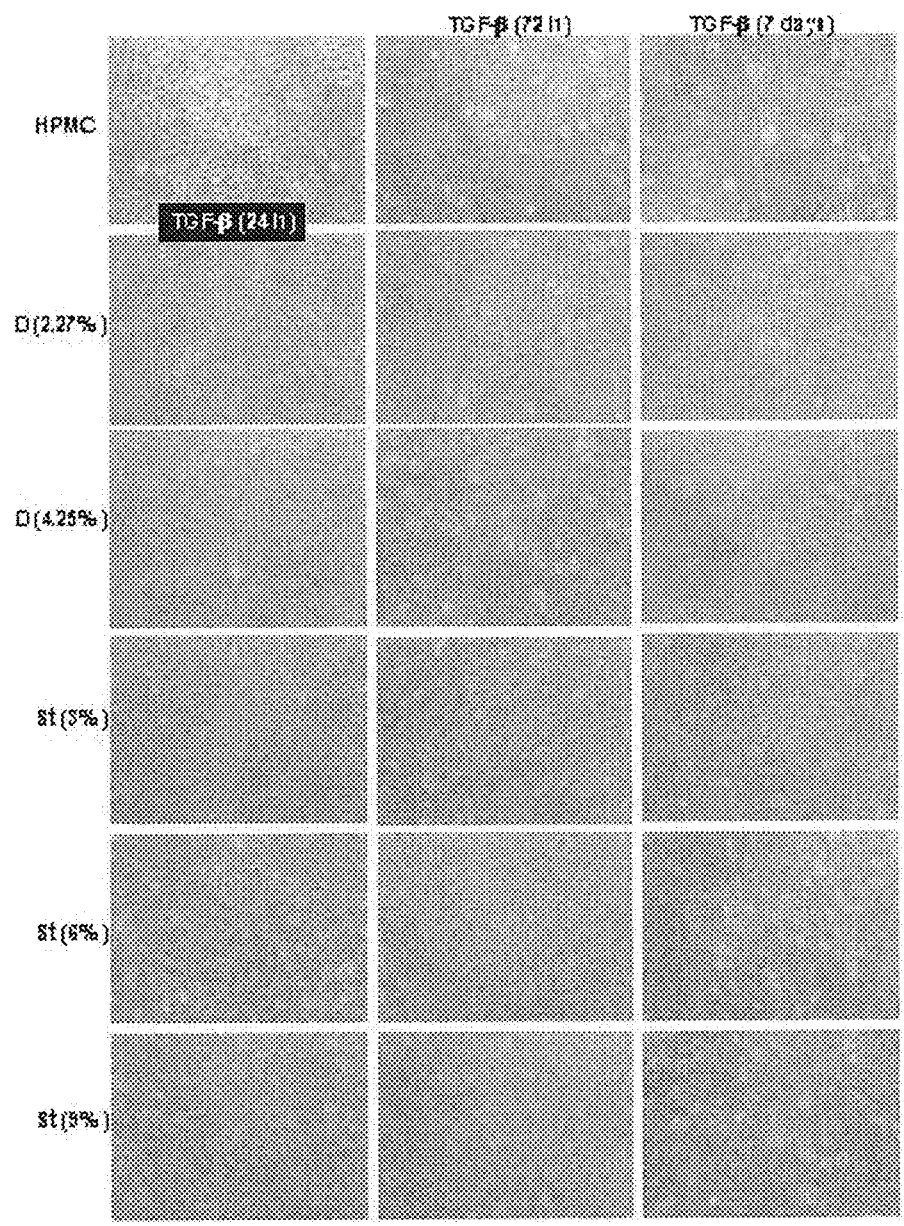

The present invention relates to pharmaceutical compositions containing steviosides and/or steviol glycosides as well as their use as osmotic agents, in particular for use in the treatment of chronic renal failure by dialysis.

Osmotically active compounds (osmotics) are used in pharmacy and medicine. For example, osmotics are used to adjust the tonicity of pharmaceutical drugs in particular parenteral medications. In doing so the osmotic pressure of a pharmaceutical drug is adjusted to be hypotonic, hypertonic or isotonic depending on how it is administered. For example, the osmotic pressure of a parenteral medicinal solution may be adjusted to match the osmotic pressure of human blood by adding an osmotic agent (isoosmotic solutions).

Furthermore osmotics are used in the treatment of renal failure by dialysis in particular in hemodialysis or peritoneal dialysis to withdraw excess water from the dialysis patient.

The peritoneal dialysis method is based on the fact that a solution containing osmotically active compounds is introduced into the abdominal cavity of a dialysis patient through a catheter. This solution is left in the patient's abdominal cavity for a certain period of time (usually a few hours) where it manifests its osmotic effect; in other words, endogenous water is withdrawn from the patient into the abdominal cavity. After a certain dwell time, the peritoneal dialysis solution, which is then diluted is drained out through a catheter.

This principle is used in various methods of peritoneal dialysis treatment. For example, the methods of intermittent peritoneal dialysis (IPD), nocturnal intermittent peritoneal dialysis (NIPD), continuous cyclic peritoneal dialysis (CCPD) or continuous ambulant peritoneal dialysis (CAPD) may be used as needed. Machines which support the patient in performing the peritoneal dialysis method are used in IPD, NIPD and CCPD. CAPD is a manual method.

Adding osmotically active compounds in particular should ensure that the osmotic pressure of the peritoneal dialysis solution is high enough during the entire dwell time in the abdominal cavity to withdraw water from the patient. In other words, water moves from the patient's circulatory system into the abdominal cavity (ultrafiltration).

However, because of the transfer of water into the abdominal cavity, there is thereby necessarily a diluting effect of the peritoneal dialysis solution introduced.

This dilution of the peritoneal dialysis solution results in a decline of the concentration of the osmotically active compound and i the end in a decline of the osmotic pressure of the solution.

If the osmotic pressure of the peritoneal dialysis solution drops due to this dilution effect, this in turn has the result that the transfer of water to the abdominal cavity per unit of time also drops or may come to a complete standstill. Thus, in these cases, there is no longer an effective withdrawal of water as the dwell time of the peritoneal dialysis solution in the patient's abdominal cavity progresses.

By absorption of osmotically active compounds into the bloodstream of the patient, the direction of the movement of water may even be reversed, i.e., water passes from the abdominal cavity into the patient's blood stream (negative ultrafiltration). This is the case when the diluted peritoneal dialysis solution in the abdominal cavity has a lower osmotic pressure than the relevant endogenous solution (for example, the non corpuscular compartment of blood) in the patient.

By adding suitable osmotically active compounds to the peritoneal dialysis solution, the osmotic pressure can be maintained over a treatment time suitable for peritoneal dialysis so that there is no excessive decline in ultrafiltration during the dwell time of the solution in the abdominal cavity. This also largely prevents any negative ultrafiltration.

The solutions used in peritoneal dialysis treatment usually contain sugar monomers or polymers, for example, glucose or polyglucose (e.g., starch derivatives) as osmotically active compounds.

BACKGROUND

U.S. Pat. No. 3,723,410 discloses a method for the extraction of stevioside from the leaves of *Stevia rebaudiana*.

U.S. Pat. No. 4,082,858 discloses a sweetening agent recovered from *Stevia rebaudiana* plant and having the chemical structure of Rebaudiosid A.

U.S. Pat. No. 4,339,433 discloses the use of compounds like ethylene-maleic acid copolymer resins, carboxymethylpolysaccharides, carboxymethylpolyvinyl alcohols as osmotic agents.

U.S. Pat. No. 4,761,237 discloses a solution for peritoneal dialysis containing a starch hydrolysate with an average degree of polymerisation of at least 4.

U.S. Pat. No. 6,770,148 discloses the use of modified icodextrins as osmotic agents in peritoneal dialysis solutions.

U.S. Pat. No. 4,649,050 relates to synthetic organic polyionic compounds and their use as osmotic agents in peritoneal dialysis solutions.

Rippe and Levin published computer simulations of ultrafiltration profiles for an icodextrin-based peritoneal fluid in CAPD (Bengt Rippe, Lars Levin, Kidney International, Vol. 57 (2000), 2546-2556). The content is hereby incorporated by reference in its entirety.

The solutions used in peritoneal dialysis treatment usually contain sugar monomers or polymers, for example, glucose or polyglucose (e.g., starch derivatives) as osmotically active compounds. It was however shown that the peritoneal membrane may undergo pathological changes under the influence of peritoneal dialysis fluids. In particular, chronic use of peritoneal dialysis fluids containing osmotic agents may result in inflammatory response, fibrotic changes and neovascularization of the peritoneal membrane and thus in a decrease or loss of the ultrafiltration capacity of the peritoneal membrane. (cf. Lazaro Gotloib, Advances in Peritoneal Dialysis, 25 (2009), 6-10; Margot Schilte et al., Peritoneal Dialysis International, 29 (2009), 605-617; Yong-Lim Kim, Peritoneal Dialysis International, 29 (2009), Suppl 2, 123-127).

The decrease in ultrafiltration capacity results in a decrease in the effectiveness of dialysis treatment and in consequence to an increased incidence of diseases such as the uraemic syndrome in dialysis patients. The decrease or loss of ultrafiltration capacity may force a discontinuation of peritoneal dialysis.

One object of this invention is to prevent or delay the pathological changes or the loss of function of the peritoneal membrane and to allow for more effective and prolonged peritoneal dialysis treatment.

A further object of this invention is to keep the ultrafiltration rate as high as possible during treatment in order to ensure a more effective dialysis treatment.

The aim is also to reduce systemic side effects that are based on the absorption of the osmotic agent into the systemic circulation of the patient.

The object of the present invention is in particular to make available osmotics which have a higher osmotic activity than traditional osmotically active compounds and are therefore suitable in particular for use in peritoneal dialysis treatment.

It is one tasks of the present invention to provide an osmotic agent which maintains its osmolarity constant over the whole dwell time.

The present invention relates to steviosides or steviol glycosides. Steviol glycosides are responsible for the sweet taste of the leaves of the *stevia* plant (*Stevia rebaudiana*). Steviol glycosides may be obtained, for example, by extraction from *stevia* plants. These compounds range in sweetness from 40 to 300 times sweeter than sucrose.

Steviol and steviol glycosides have the chemical structure of general formula I, wherein R1 and R2 are either H or glucose, xylose or rhamnose units.

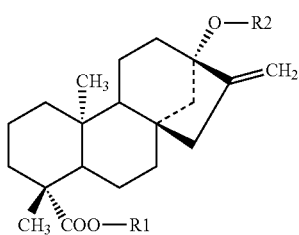

I

Steviol glycosides are based on the tetracyclic ent-kauran-diterpene steviol which is the aglycone and wherein R1 and R2 of formula I represent hydrogen.

Steviol glycosides are formed by replacing steviol's carboxyl hydrogen atom with glucose to form an ester, and replacing the hydroxyl hydrogen with combinations of glucose, xylose and rhamnose to form an ether. Some naturally occurring steviol glycosides are summarized in table 1.

TABLE 1

| Steviol glycosides | | |
|---|---|---|
| Compound | R1 | R2 |
| Steviol | H | H |
| Steviolbiosid | H | β-glc-β-glc (2→1) |
| Steviosid | β-glc | β-glc-β-glc (2→1) |
| Rebaudiosid A | β-glc | β-glc-β-glc (2→1)<br>\|<br>β-glc (3→1) |
| Rebaudiosid B | H | β-glc-β-glc (2→1)<br>\|<br>β-glc (3→1) |
| Rebaudiosid C | β-glc | β-glc-α-rha (2→1)<br>\|<br>β-glc (3→1) |
| Rebaudiosid D | β-glc-β-glc (2→1) | β-glc-β-glc (2→1)<br>\|<br>β-glc (3→1) |
| Rebaudiosid E | β-glc-β-glc (2→1) | β-glc-β-glc (2→1) |

TABLE 1-continued

| Steviol glycosides | | |
|---|---|---|
| Compound | R1 | R2 |
| Rebaudiosid F | β-glc | β-glc-xyl (2→1)<br>\|<br>β-glc (3→1) |
| Dulkosid A | β-glc | β-glc-α-rha (2 →1) |

(glc = glucose, rha = rhamnose, xyl = xylose)

One object of the present invention is to make available steviol glycoside derivatives having high water solubility, an improved osmotic efficacy and an increased ultrafiltration in comparison with osmotic agents of the prior art and which are thus suitable for pharmaceutical compositions and dialysis, in particular for peritoneal dialysis treatment.

In particular the efficacy of the inventive steviol glycoside derivatives may be attributed to defined compounds and is not based on the effects of a complex mixture of a wide variety of different starch derivatives. This also increases safety for the patient and in particular facilitates the evaluation of pharmacological and/or clinical data.

This object is achieved by the subject matter of the patent claims.

The present invention also relates to steviol glycoside derivatives of the general structure I wherein R1 and R2 independently denote either H, or a linear or branched $C_1$ to $C_6$ alkyl group, or a polyethylene glycol unit —$CH_2$—($CH_2$—O—$CH_2$—)$_n$—$CH_2$—OH with n being an integer from 0 to 500, or one or more glucose, xylose or rhamnose units for use as an osmotic agent.

One embodiment of the present invention relates to steviol glycoside derivatives of the general structure I wherein R1 and/or R2 independently are a polyethylene glycol unit of the general formula II with n being an integer from 0 to 500:

$$—(CH_2—CH_2—O—)_n—CH_2—CH_2—OH \qquad II$$

One embodiment of the present invention relates to steviol glycoside derivatives of the general structure I wherein R1 and/or R2 independently are a methyl, ethyl, n-propyl, iso-propyl, n-butyl, sec-butyl, tert.-butyl, n-pentyl, iso-pentyl, neo-pentyl, n-hexyl, iso-hexyl neo-hexyl, 3-methylpentyl, or 2,3-dimethyl butyl group.

One preferred embodiment of the present invention relates to steviol glycoside derivatives of the general structure I wherein R1 is an alkyl group, preferably a methyl, ethyl, n-propyl, iso-propyl, n-butyl, sec-butyl, tert.-butyl, n-pentyl, iso-pentyl, neo-pentyl, n-hexyl, iso-hexyl neo-hexyl, 3-methylpentyl, or 2,3-dimethyl butyl group, most preferred a methyl or ethyl group, or a polyethylene group of general formula II, with n being an integer from 0 to 500, more preferred n=0-100, most preferred n=0-50, especially n=0, and R2 is one, two or three glucose, rhamnose or xylose units, preferably one, two or three glucose units most preferably [β-D-glucopyranosyl (1→2)-β-D-glucopyranosyl]-units or [2-O-β-D-glucopyranosyl-3-O-β-D-glucopyranosyl-β-D-glucopyranosyl]-units.

Three preferred steviol glycoside derivates are 19-O-Methyl-13-O-(beta-glucopyranosyl(1-2)-beta-glucopyranosyl(1-3))-beta-glucopyranosyl-13-hydroxykaur-16-en-19-oic acid, 19-O-Ethyl-13-O-(beta-glucopyranosyl(1-2)-beta-g lucopyranosyl(1-3))-beta-glucopyranosyl-13-hydroxykaur-16-en-19-oic acid, and 19-O-(2'-hydroxyethyl)-13-O-(beta-glucopyranosyl(1-2)-betaglucopyranosyl(1-3))-beta-glucopyranosyl-13-hydroxykaur-16-en-19-oic acid.

FIGURES

FIG. 1 shows microscopic photographs of mesothelial cells either exposed to PD solutions based on glucose (2.27 wt. % and 4.25 wt. %) or based on steviolglycosides (ST) (3 wt. %, 6 wt. % and 9 wt. %) at 72 h and at 7 days after stimulation of epithelial-to-mesenchymal transition (EMT) by TGF-β.

Figure 2:
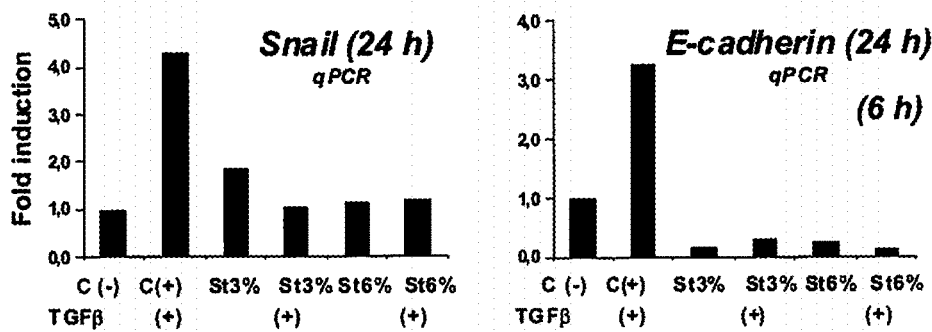

FIG. 2 compares the effect of steviolglycoside- and glucose-based PD fluids on gene expression pattern of typical markers for epithelial-to-mesenchymal transition (EMT) of mesothelial cells in vitro with and without the addition of TGF-β.

Figure 3:
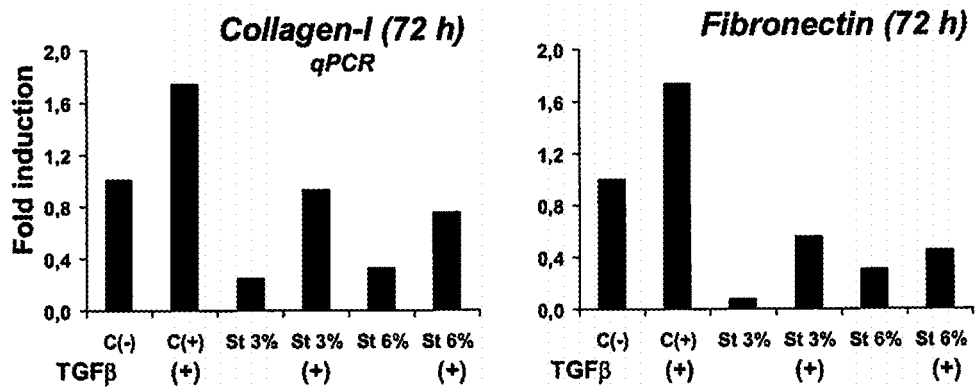

FIG. 3 shows the effect of steviolglycoside PD fluids on EMT of mesothelial cells in vitro. Collagen-I and fibronectin do not increase in spite of TGF-β stimulus.

Figure 4:
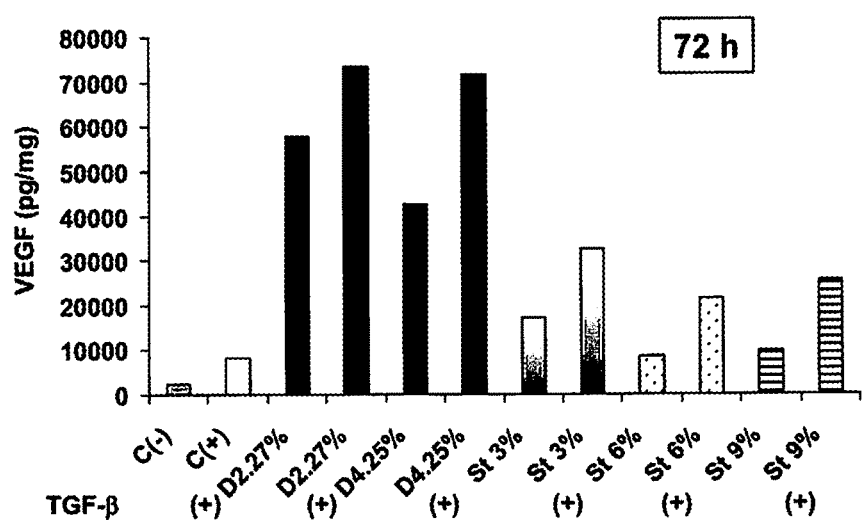

FIG. 4 compares the effect of steviolglycoside (ST) (3 wt. %, 6 wt. % and 9 wt. %) and glucose-based PD fluids (2.27 wt. % and 4.25 wt. % glucose) on the production of VEGF by mesothelial cells in vitro without (left columns) and with (right columns (+)) TGF-β stimulus.

Figure 5:
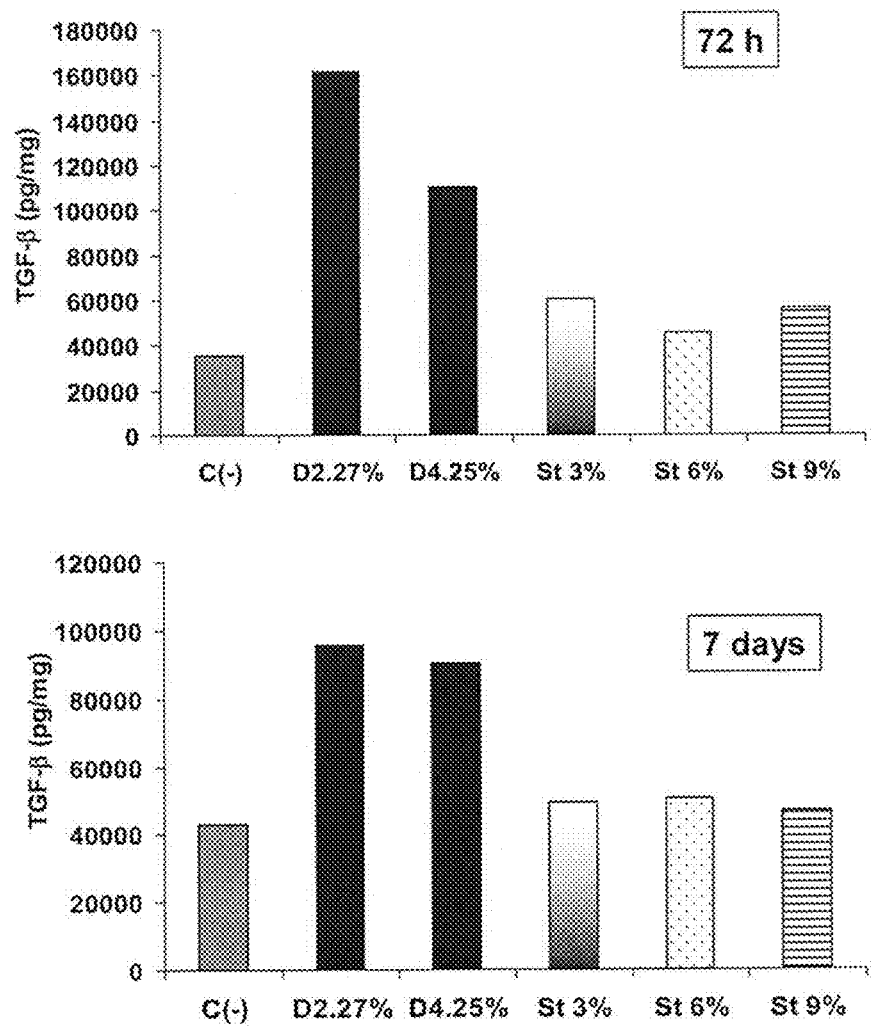

FIG. 5 compares the in vitro effect of steviolglycoside and glucose-based PD fluids on the production of TGF-β by mesothelial cells.

Figure 6:
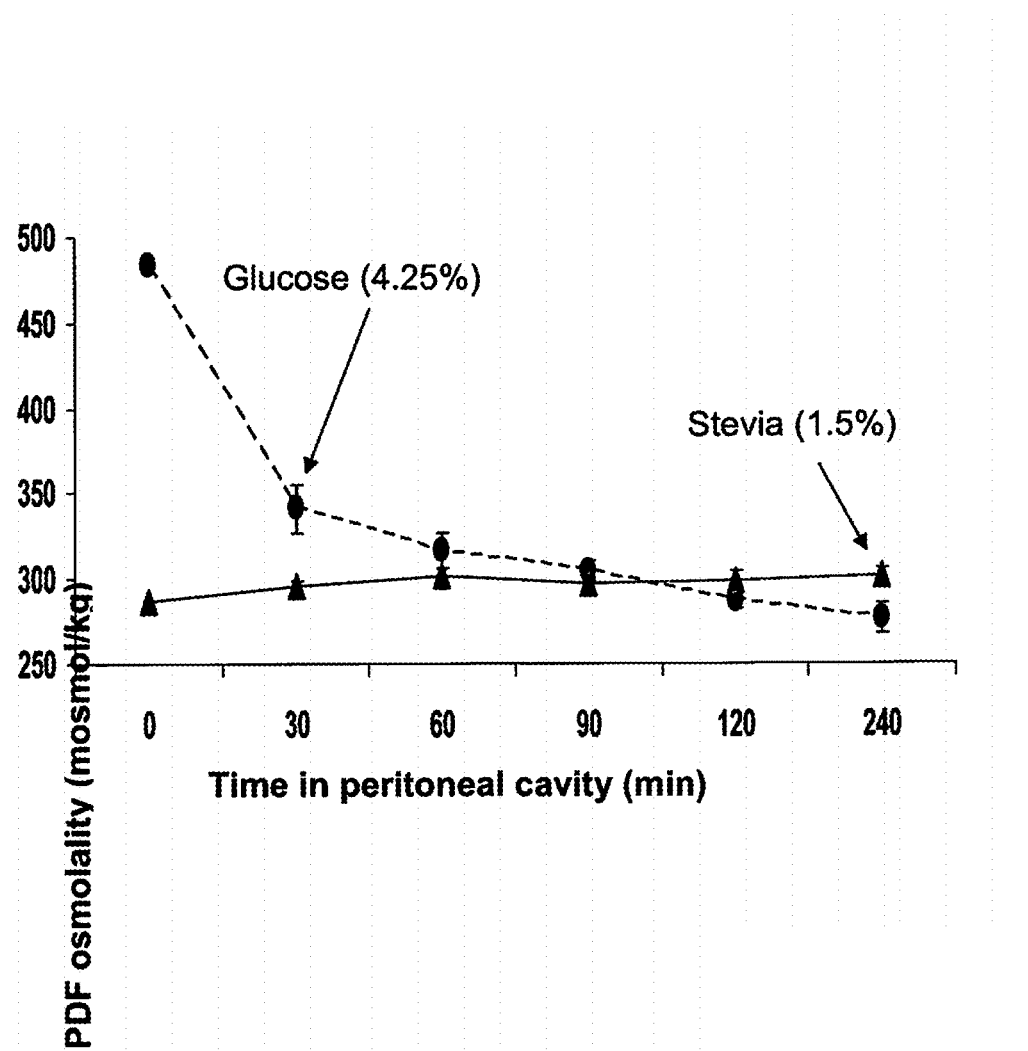

FIG. 6 compares the intraperitoneal osmolality of glucose-based (4.25 wt. % glucose) and *stevia*-based (1.5 wt. %) PD fluids at various dwell times in the rat model.

Figure 7:
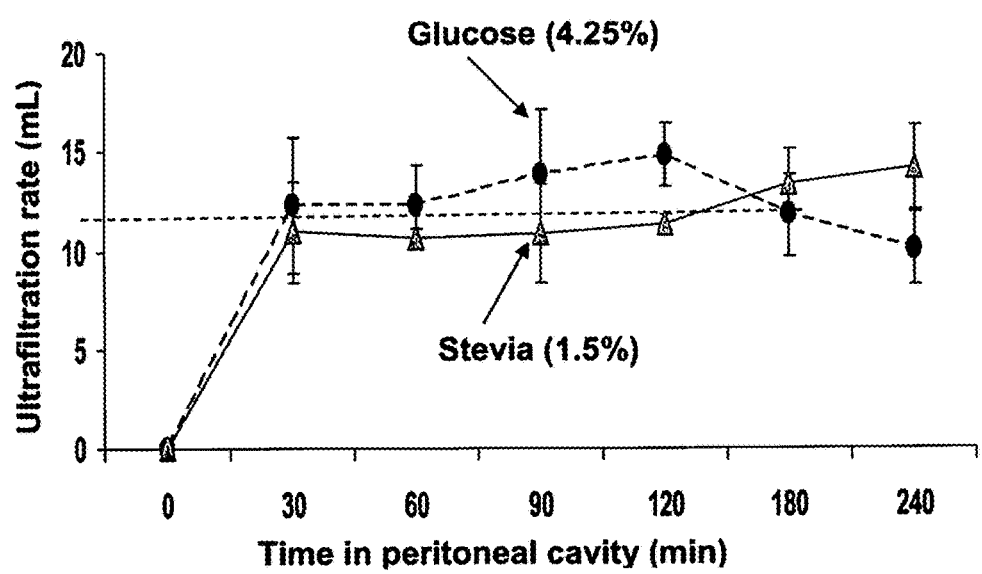

FIG. 7 compares the ultrafiltration rate of glucose-based (4.25 wt. % glucose) and *stevia*-based (1.5 wt. %) PD fluids at various dwell times in the rat model. The red line indicates the instilled volume.

Figure 8:
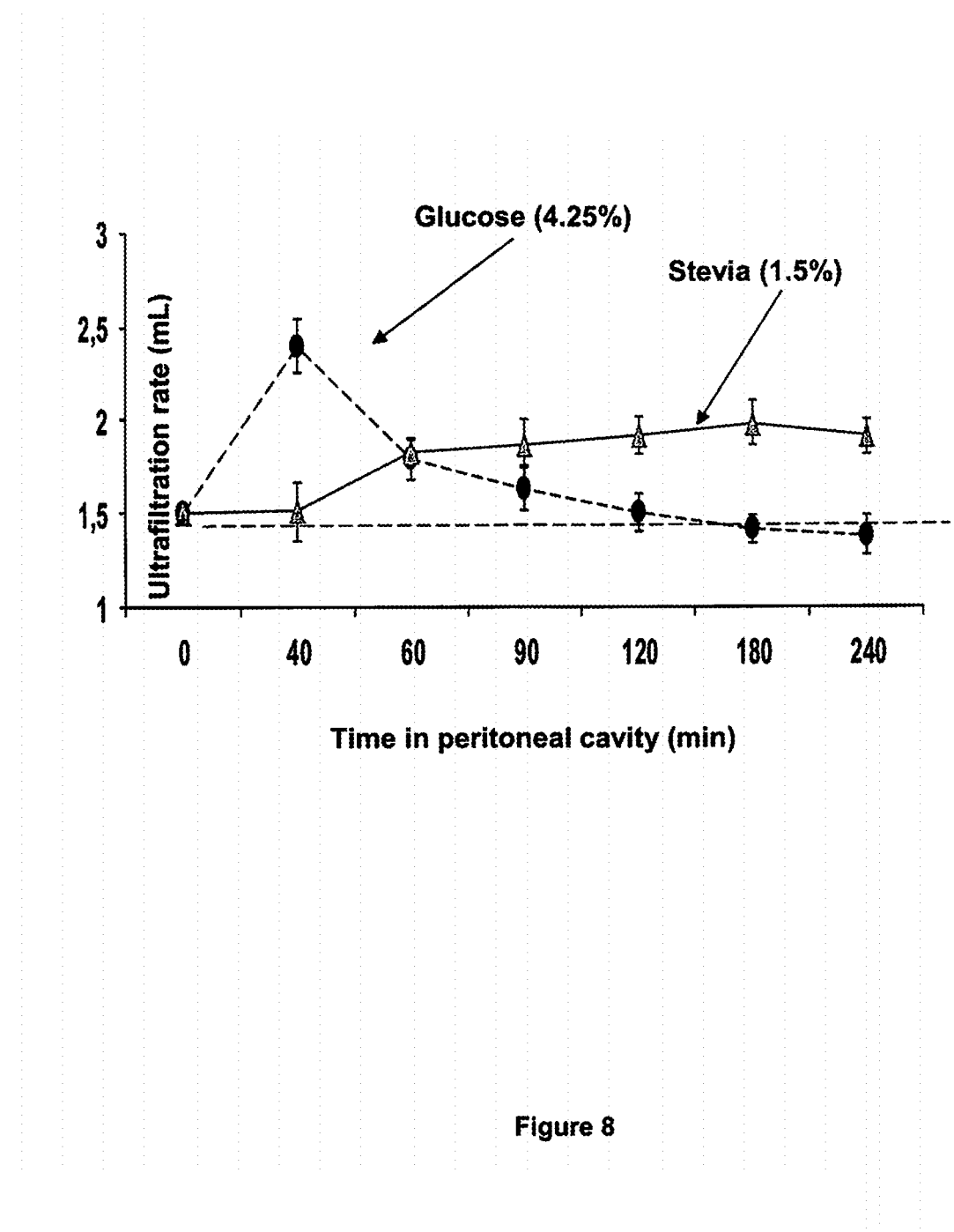

FIG. 8 compares the ultrafiltration rate of glucose-based (4.25 wt. % glucose) and *stevia*-based (1.5 wt. %) PD fluids at various dwell times in the mouse model. The red line indicates the instilled volume.

Figure 9:
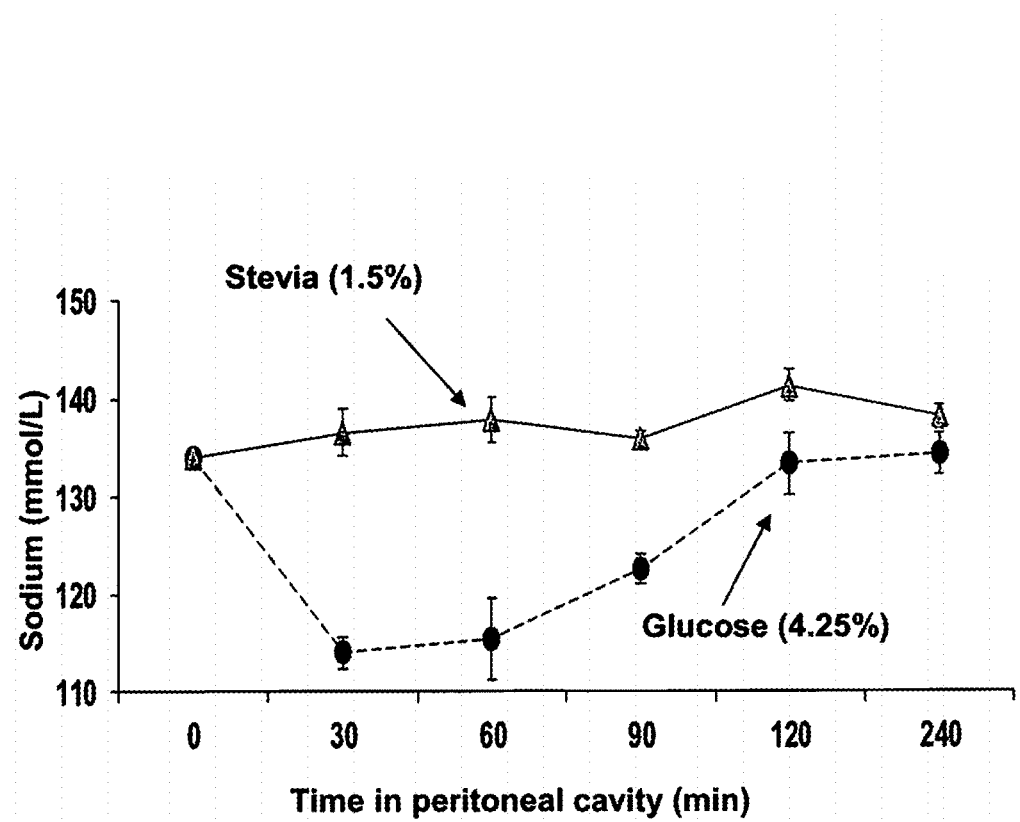

FIG. 9 compares the sodium concentration of glucose-based (4.25 wt. % glucose) and *stevia*-based (1.5 wt. %) PD fluids at various dwell times in the rat model.

For the purpose of this description, the term "theoretical osmolarity" stands for the osmolarity calculated theoretically. Those skilled in the art are familiar with the methods of calculating this value.

For the purpose of this description the term "colloid osmotic pressure" stands for the experimentally measured osmotic pressure of the solution which is composed of the osmotic pressure and the oncotic pressure. Suitable methods of determining this value experimentally are familiar to those skilled in the art.

For the purpose of this description the term "osmolality" stands for the osmolality of the solution determined experimentally by means of the reduction in freezing point. Methods of determining the freezing point reduction are familiar to those skilled in the art.

The inventive steviol glycoside derivatives are preferably suitable as osmotic agents for adjusting the tonicity of pharmaceutical drugs, in particular medicinal solutions for parenteral administration.

In a preferred embodiment, the inventive steviol glycoside derivatives are used in the dialysis treatment, preferably in hemodialysis and/or peritoneal dialysis treatment.

The inventive steviol glycoside derivatives are suitable in particular for use in peritoneal dialysis treatment.

Another subject matter of this invention relates to dialysis solutions containing at least one inventive steviol glycoside or an inventive steviol glycoside derivative.

In a preferred embodiment, the inventive dialysis solution is a hemodialysis solution or a peritoneal dialysis solution. The inventive dialysis solution is in particular a peritoneal dialysis solution.

Dosage forms used in the dialysis treatment are preferably concentrates in multicomponent systems or ready-to-use dialysis solutions.

For the purposes of this invention the term "dialysis solution" comprises a ready-to-use dosage form for the dialysis treatment, i.e., a liquid preparation which is suitable as such for administration. In particular the dialysis solution need not be diluted and/or mixed with other preparations prior to administration.

In contrast with the dialysis solutions described above, concentrates which may be present either in liquid, semi-solid or solid form are diluted with water or aqueous solutions prior to administration or they are dissolved in water or aqueous solutions. Similarly the component of a multicomponent system must be mixed together prior to administration in order to obtain a ready-to-use dialysis solution. Concentrates and multicomponent systems may thus be regarded as the precursor of the inventive dialysis solution.

The inventive dialysis solution is preferably a hemodialysis solution or a peritoneal dialysis solution. Hemodialysis and peritoneal dialysis solutions usually contain electrolytes in a concentration which corresponds essentially to the plasma electrolyte concentration. Electrolytes usually include sodium, potassium (only for hemodialysis), calcium, magnesium and chloride ions.

Dialysis solutions usually have a physiologically tolerable pH. This is preferably achieved by using buffers (buffer systems) which may even contribute to the total electrolyte content. The buffers are preferably bicarbonate, lactate or pyruvate.

Furthermore dialysis solutions usually have a physiologically tolerable osmolarity. This is usually achieved by the electrolyte contained in the dialysis solution, any osmotic agent and the inventive steviol glycoside derivatives which are physiologically tolerable as osmotically active compounds (osmotics) in the desired concentration.

The inventive dialysis solution has an osmolarity in the range of preferably 200 to 550 mOsm/L.

In the case when the inventive dialysis solution is a hemodialysis solution, the osmolarity is preferably 200 to 350 mOsm/L or 210 to 340 mOsm/L, more preferably 220 to 330 mOsm/L, even more preferably 230 to 320 mOsm/L, most preferably 240 to 310 mOsm/L and in particular 250 to 300 mOsm/L. Methods of measuring the osmolarity and the osmotic pressure are familiar to those skilled in the art. For example, these may be determined with the help of a membrane osmometer or other suitable measurement methods.

In the case when the inventive dialysis solution is a peritoneal dialysis solution, the osmolarity is preferably 200 to 570 mOsm/L or 210 to 560 mOsm/L, more preferably 220 to 550 mOsm/L, even more preferably 230 to 540 mOsm/L, most preferably 240 to 530 mOsm/L and in particular 250 to 520 mOsm/L. In a preferred embodiment, the osmolarity is 250±50 mOsm/L or 250±45 mOsm/L, more preferably 250±35 mOsm/L, even more preferably 250±25 mOsm/L, most preferably 250±15 mOsm/L and in particular 250±10 mOsm/L. In another preferred embodiment, the osmolarity is 300±50 mOsm/L or 300±45 mOsm/L, more preferably 300±35 mOsm/L, even more preferably 300±25 mOsm/L, most preferably 300±15 mOsm/L and in particular 300±10 mOsm/L. In another preferred embodiment, the osmolarity is 350±50 mOsm/L or 350±45 mOsm/L, more preferably 350±35 mOsm/L, even more preferably 350±25 mOsm/L, most preferably 350±15 mOsm/L and in particular 350±10 mOsm/L. In another preferred embodiment, the osmolarity is 400±50 mOsm/L or 400±45 mOsm/L, more preferably 400±35 mOsm/L, even more preferably 400±25 mOsm/L, most preferably 400±15 mOsm/L and in particular 300±10 mOsm/L. In another preferred embodiment, the osmolarity is 450±50 mOsm/L or 450±45 mOsm/L, more preferably 450±35 mOsm/L, even more preferably 450±25 mOsm/L, most preferably 450±15 mOsm/L and in particular 450±10 mOsm/L. In another preferred embodiment, the osmolarity is 500±50 mOsm/L or 500±45 mOsm/L, more preferably 500±35 mOsm/L, even more preferably 500±25 mOsm/L, most preferably 500±15 mOsm/L and in particular 500±10 mOsm/L.

The inventive dialysis solution has a pH of preferably 4.0 to 8.0, more preferably from 4.2 to 7.5, even more preferably from 4.4 to 6.8, most preferably from 4.6 to 6.0 or 4.8 to 5.5 and in particular from 5.0 to 5.2 or 5.0±0.1; measured at room temperature (20 to 23° C.). In a preferred embodiment, the pH is 4.8±1.0 or 4.8±0.8, more preferably 4.8±0.7 or 4.8±0.6, even more preferably 4.8±0.5 or 4.8±0.4, most preferably 4.8±0.3 or 4.8±0.2 and in particular 4.8±0.1. In a preferred embodiment, the pH is 5.0±1.0 or 5.0±0.8, more preferably 5.0±0.7 or 5.0±0.6, even more preferably 5.0±0.5 or 5.0±0.4, most preferably 5.0±0.3 or 5.0±0.2 and in particular 5.0±0.1. In a preferred embodiment, the pH is 5.2±1.0 or 5.2±0.8, more preferably 5.2±0.7 or 5.2±0.6, even more preferably 5.2±0.5 or 5.2±0.4, most preferably 5.2±0.3 or 5.2±0.2 and in particular 5.2±0.1. In a preferred embodiment, the pH is 5.5±1.0 or 5.5±0.8, more preferably 5.5±0.7 or 5.5±0.6, even more preferably 5.5±0.5 or 5.5±0.4, most preferably 5.5±0.3 or 5.5±0.2 and in particular 5.5±0.1. In a preferred embodiment, the pH is 6.0±1.0 or 6.0±0.8, more preferably 6.0±0.7 or 6.0±0.6, even more preferably 6.0±0.5 or 6.0±0.4, most preferably 6.0±0.3 or 6.0±0.2 and in particular 6.0±0.1. In a preferred embodiment, the pH is 6.5±1.0 or 6.5±0.8, more preferably 6.5±0.7 or 6.5±0.6, even more preferably 6.5±0.5 or 6.5±0.4, most preferably 6.5±0.3 or 6.5±0.2 and in particular 6.5±0.1. In a preferred embodiment, the pH is 7.0±1.0 or 7.0±0.8, more preferably 7.0±0.7 or 7.0±0.6, even more preferably 7.0±0.5 or 7.0±0.4, most preferably 7.0±0.3 or 7.0±0.2 and in particular 7.0±0.1. In a preferred embodiment, the pH is 7.4±1.0 or 7.4±0.8, more preferably 7.4±0.7 or 7.4±0.6, even more preferably 7.4±0.5 or 7.4±0.4, most preferably 7.4±0.3 or 7.4±0.2 and in particular 7.4±0.1. In a preferred embodiment, the pH is 8.0±1.0 or 8.0±0.8, more preferably 8.0±0.7 or 8.0±0.6, even more preferably 8.0±0.5 or 8.0±0.4, most preferably 8.0±0.3 or 8.0±0.2 and in particular 8.0±0.1.

The inventive dialysis solution contains one or more steviol glycoside derivative in a total concentration of preferably 0.001 mM to 10 M or 0.01 to 1.0 M, more preferably 0.10 to 500 mM, even more preferably 1.0 to 250 mM, most preferably 10 to 100 mM and in particular 25 to 90 mM. In a preferred embodiment, the total concentration is 25±24 mM, more preferably 25±20 mM, even more preferably 25±15 mM, most preferably 25±10 mM and in particular 25±5 mM. In another preferred embodiment, the total concentration is 50±25 mM, more preferably 50±20 mM, even more preferably 50±15 mM, most preferably 50±10 mM and in particular 50±5 mM. In another preferred embodiment, the total concentration is 75±25 mM, more preferably 75±20 mM, even more preferably 75±15 mM, most preferably 75±10 mM and in particular 75±5 mM. In another preferred embodiment, the total concentration is 100±25 mM, more preferably 100±20 mM, even more preferably 100±15 mM, most preferably 100±10 mM and in particular 100±5 mM. In another preferred embodiment, the total concentration is 200±25 mM, more preferably 200±20 mM, even more preferably 200±15 mM, most preferably 200±10 mM and in particular 200±5 mM. The total concentration is preferably calculated by means of the average molecular weight of the inventive steviol glycoside derivatives.

The inventive dialysis solution contains an inventive steviol glycoside derivative in a total weight concentration of preferably 0.01 g/L to 1.0 kg/L, more preferably from 0.1 to 750 g/L, even more preferably from 1.0 to 500 g/L, most preferably 10 to 250 g/L and in particular from 100 to 200 g/L. In a preferred embodiment, the total weight concentration is 25±24 g/L, more preferably 25±20 g/L, even more preferably 25±15 g/L, most preferably 25±10 g/L and in particular 25±5 g/L. In another preferred embodiment, the total weight concentration is 50±25 g/L, more preferably 50±20 g/L, even more preferably 50±15 g/L, most preferably 50±10 g/L and in particular 50±5 g/L. In another preferred embodiment, the total weight concentration is 75±25 g/L, more preferably 75±20 g/L, even more preferably 75±15 g/L, most preferably 75±10 g/L and in particular 75±5 g/L. In another preferred embodiment, the total weight concentration is 100±25 g/L, more preferably 100±20 g/L, even more preferably 100±15 g/L, most preferably 100±10 g/L and in particular 100±5 g/L. In another preferred embodiment, the total weight concentration is 200±25 g/L, more preferably 200±20 g/L, even more preferably 200±15 g/L, most preferably 200±10 g/L and in particular 200±5 g/L.

The inventive dialysis solution may also contain other osmotically active substances, for example, glucose, polyglucose, crosslinked glucose or polyglucose, mannitol, glycerol, or amino acids.

The inventive dialysis solution preferably contains one or more electrolytes.

The term "electrolyte" in the sense of this invention stands for a substance containing free ions and having electrical conductivity. The electrolyte preferably dissociates completely into cations and anions without making any significant change in the pH of an aqueous composition. This property differentiates electrolytes from buffer substances. The electrolytes are preferably present in a concentration which results in essentially complete dissociation in water.

Preferred electrolytes are selected from the group of alkali metals such as $Na^+$ and $K^+$ and the alkaline earth metals such as $Ca^{2+}$ and $Mg^{2+}$. $Cl^-$ is a preferred anion.

The inventive dialysis solution that contains additional anions, for example, bicarbonate, dihydrogen phosphate, hydrogen phosphate, phosphate, acetate, lactate and pyruvate; however, these anions (in suitable combinations with cations) are not referred to as electrolytes within the sense of the present invention but instead are referred to as buffers because of their buffering capacity.

In a preferred embodiment, the inventive dialysis solution contains $Na^+$ ions. The concentration of $Na^+$ ions is preferably 10 to 200 mM or 50 to 160 mM, more preferably 100 to 150 mM or 110 to 140 mM, even more preferably 115 to 140 mM or 120 to 140 mM, most preferably 120 to 135 mM and in particular 120 to 130 mM. In one preferred embodiment, the inventive dialysis solution contains 121 to 126 mM of sodium. In another preferred embodiment, the inventive dialysis solution does not contain any Na ions.

In a preferred embodiment, the inventive dialysis solution contains $K^+$ ions. The concentration of $K^+$ ions is preferably 0.10 to 20 mM, more preferably 0.25 to 15 mM, even more preferably 0.50 to 10 mM, most preferably 0.75 to 7.5 mM and in particular 1.0 to 5.0 mM. In another preferred embodiment, the concentration of $K^+$ ions is $1.0 \pm 0.75$, $2.0 \pm 0.75$, $3.0 \pm 0.75$, $4.0 \pm 0.75$ or $5.0 \pm 0.75$ mM and in particular $1.0 \pm 0.50$, $2.0 \pm 0.50$, $3.0 \pm 0.50$, $4.0 \pm 0.50$ or $5.0 \pm 0.50$. In another preferred embodiment, the inventive dialysis solution does not contain any $K^+$ ions.

In a preferred embodiment, the inventive dialysis solution contains $Ca^{2+}$ ions. The concentration of $Ca^{2+}$ ions is preferably 0.1 to 10 mM, more preferably 0.25 to 8 mM, even more preferably 0.5 to 7.5 mM, most preferably 0.75 to 2.25 mM and in particular 1 to 2 mM. In another preferred embodiment, the concentration of $Ca^{2+}$ ions is 0.25, 0.5, 0.75, 1, 1.25, 1.5, 1.75 or 2 mM. In another preferred embodiment, the inventive dialysis solution does not contain any $Ca^{2+}$ ions.

In a preferred embodiment, the inventive dialysis solution contains $Mg^{2+}$ ions. The concentration of $Mg^{2+}$ ions is preferably 0.01 to 1 mM, more preferably 0.05 to 0.75 mM, even more preferably 0.1 to 0.5 mM, most preferably 0.15 to 0.4 mM and in particular 0.2 to 0.3 mM. In another preferred embodiment, the concentration of $Mg^{2+}$ ions is 0.05, 0.075, 0.1, 0.2, 0.25, 0.50 or 0.75 mM. In another preferred embodiment, the inventive dialysis solution does not contain any $Mg^{2+}$ ions.

In a preferred embodiment, the inventive dialysis solution contains $Cl^-$ ions. The concentration of $Cl^-$ ions is preferably 10 to 300 mM, more preferably 25 to 250 mM, even more preferably 50 to 200 mM, most preferably 75 to 150 mM and in particular 80 to 125 mM. In another preferred embodiment, the concentration of $Cl^-$ ions is $100 \pm 50$ mM, more preferably $100 \pm 25$ mM, most preferably $100 \pm 10$ mM and in particular $96 \pm 4$ mM. In another preferred embodiment, the inventive dialysis solution does not contain any $Cl^-$ ions.

The inventive dialysis solution preferably contains one or more buffers.

Suitable buffers are familiar to those skilled in the art. Buffers usually include lactate, bicarbonate, carbonate, dihydrogen phosphate, hydrogen phosphate, phosphate, pyruvate, citrate, isocitrate, succinate, fumarate, acetate and lactate salts. Those skilled in the art know that the corresponding cation of the aforementioned anions is a component of the buffer which is used to adjust the pH (e.g., $Na^+$ as a component of the buffer $NaHCO_3$). However, if the buffer salt has dissociated in water it also has the effect of an electrolyte. For the purposes of this description the concentrations of cations or anions and the total concentration of anions are calculated regardless of whether they are used as component of electrolytes, buffers or other compounds (e.g., as salts of the inventive steviol glycoside derivatives).

In a preferred embodiment, the buffer contains bicarbonate. Bicarbonate is a well-tolerated buffer system, which is in equilibrium with carbonate in an alkaline medium and is in equilibrium with $H_2CO_3$ or $CO_2$ in an acidic medium. Other buffer systems may also be used in addition to bicarbonate if they have a buffering effect in the pH range of pH 4 to pH 9.5, more preferably in the range of pH 5 to pH 7.6 and in particular in the range of pH 7.6, 7.4, 7.2 and/or 7.0; for example, this also includes compounds such as lactate or pyruvate that can be metabolized to bicarbonate in the body.

In another preferred embodiment, the buffer contains the salt of a weak acid preferably lactate. The acid strength (pKs) of the weak acid is preferably ≤5. The buffer may also be a mixture of substances having a buffering effect, e.g., a mixture containing bicarbonate and a salt of a weak acid (e.g., lactate). A low bicarbonate concentration has the advantage that the $CO_2$ pressure in the container is low.

In a preferred embodiment, the inventive dialysis solution is buffered by bicarbonate. The bicarbonate concentration is preferably 1.0 to 200 mM, more preferably 2.5 to 150 mM, even more preferably 5 to 100 mM, most preferably 5 to 75 mM or 10 to 50 mM and in particular 20 to 30 mM. In another preferred embodiment, the bicarbonate concentration is 25 mM. In another preferably embodiment the inventive dialysis solution contains no bicarbonate.

In a preferred embodiment, the inventive dialysis solution is buffered by lactate. The lactate concentration is preferably 1.0 to 200 mM, more preferably 2.5 to 150 mM, even more preferably 5 to 100 mM, most preferably 10 to 50 mM or 10 to 25 mM and in particular 15 mM. In another preferred embodiment, the inventive dialysis solution contains no lactate.

In a preferred embodiment, the inventive dialysis solution is buffered by acetate. The acetate concentration is preferably 1.0 to 100 mM, more preferably 1.0 to 50 mM, even more preferably 1.0 to 25 mM, most preferably 1.0 to 10 mM or 2.0 to 7.5 mM and in particular 2.5 to 7.0 mM. In another preferred embodiment, the inventive dialysis solution contains no acetate.

The total volume of dialysis solution is not limited. The volume usually amounts to several liters (suitable administration volume for one patient) up to a few hundred liters (suitable supply volume for more than one patient).

As already explained above, the term "dialysis solution" in the sense of this invention is to be understood to refer to a ready-to-use dialysis solution, i.e., the dialysis solution may be used directly for the dialysis treatment (hemodialysis or peritoneal dialysis).

In a preferred embodiment, the inventive dialysis solution is a peritoneal dialysis solution as described below.

The peritoneal dialysis solution is biochemically formulated so that it essentially corrects the metabolic acidosis condition associated with renal failure. The peritoneal dialysis solution preferably contains bicarbonate in approximately physiological concentrations. In a preferred embodiment, the peritoneal dialysis solution contains bicarbonate in a concentration of approximately 20 to 34 mM. In another preferred embodiment, the peritoneal dialysis solution contains a bicarbonate concentration of 25 mM.

Furthermore the peritoneal dialysis solution preferably contains carbon dioxide with a partial pressure ($pCO_2$) of less than 80 mmHg. In a preferred embodiment, the $p_{CO2}$ of the peritoneal dialysis solution is essentially equal to the $p_{CO2}$ measured in blood vessels.

Furthermore the peritoneal dialysis solution preferably has a pH of approximately 7.4. Therefore the peritoneal dialysis solution is a physiologically tolerable solution.

The peritoneal dialysis solution preferably contains a weak acid with a pKs≤5. The weak acids are preferably compounds which occur as physiological metabolites in the glucose metabolism. The weak acid is preferably selected from the group consisting of lactate, pyruvate, citrate, isocitrate, ketoglutarate, succinate, fumarate, malate and oxaloacetate. These acids may either be present alone or as a mixture in the peritoneal dialysis solution. The weak acids are preferably present in a concentration of 10 to 20 mEq/L and essentially as sodium salts in the peritoneal dialysis solution. The weak acid is preferably present in the peritoneal dialysis solution in an amount corresponding to the daily metabolic hydrogen production of approximately 1 mEq/kg per day. The peritoneal dialysis solution contains at least one steviol glycoside or a steviol glycoside derivative as defined above.

The inventive peritoneal dialysis solution preferably has a bicarbonate concentration and a $pCO_2$ like those measured in healthy patients not in renal failure, e.g., 35-45 mmHg. The weak acid diffuses along the concentration gradient from the dialysis solution into the blood of the dialysis patient and thus corrects the metabolic acidosis of the dialysis patient.

Another subject matter of this invention relates to multicomponent systems for preparing the ready-to-use dialysis solutions described above. The preparation preferably takes place in a manner which is described in detail, i.e., by following a corresponding instruction (protocol). Said preparation may be performed manually, e.g., by mixing individual components or diluting one component with water. However, the preparation may also take place in an automated fashion, e.g., by means of an apparatus which is suitable for this process and may be commercially available. The preparation need not necessarily lead to a dialysis solution with a static (uniform) composition but instead may also lead to a dialysis solution which undergoes a continuous change in its composition, and this change can be monitored by a suitable device. For example, the inventive steviol glycoside may be present in a dialysis solution, which is diluted continuously during the dialysis treatment, so that the patient is exposed to a decreasing concentration of steviol glycoside.

In a preferred embodiment, the inventive dialysis solutions are suitable for use in the treatment of renal failure.

In another preferred embodiment, the inventive dialysis solutions are suitable for use in dialysis treatment.

In another preferred embodiment, the inventive dialysis solutions are suitable for use in hemodialysis and/or peritoneal dialysis treatment.

Another subject matter of this invention relates to a kit which is configured for preparing the inventive dialysis solutions, such that the kit comprises
  a first component,
  a second component, and
  optionally an additional component or several additional components, and
  the inventive dialysis solution is prepared by mixing the first component with the second component and optionally the additional component(s).

The kit comprises at least one first component and one second component. The kit may also comprise additional components, for example, a third component and a fourth component. The kit preferably consists of three components, which are preferably different from one another.

In the sense of this invention the term "component" preferably comprises liquid, semisolid or solid compositions which may be the same as one another or different from one another, such that by mixing all the components of the kits, the inventive ready-to-use dialysis solution is obtained. An individual component preferably contains part of the ingredients which are contained in the ready-to-use dialysis solution.

The first and second components may independently of one another be solid, semisolid or liquid. In the case when the components are liquid, they may be solutions or dispersions (e.g., dispersions or suspensions).

In a preferred embodiment, the first component is liquid, preferably pure water or an aqueous solution, and the second component is also liquid. In another preferred embodiment, the first component is liquid preferably pure water or an aqueous solution and the second component is solid preferably a powdered mixture.

The first component is preferably a solution containing osmotically active substances (e.g., inventive steviol glycoside derivatives), calcium ions, magnesium ions, hydronium ions and chloride ions.

The inventive kit may be embodied in various ways. For example, the individual components may be present in separate containers (e.g., individual bags). However, the inventive kit is preferably a container, for example, a multichamber container system (e.g., flexible or rigid multichamber contain system), preferably a flexible multichamber bag system. The inventive kit is preferably a multichamber container system which contains the first component, the second component and optionally one or more additional components in chambers which are separated from one another by soluble and/or breakable separation systems (e.g., breakable dividing parts) such that the first component, the second component and optionally the one or more additional components can be mixed together with one another after dissolving and/or breaking the separation system in order to obtain the inventive dialysis solution.

The multichamber container may be in the form of a plastic container (e.g., a multichamber plastic bag) comprising a separate chamber for each individual component. The plastic container preferably holds the individual component solutions in chambers, each being separated from the others by dividing elements.

The multichamber container is preferably a two-chamber bag comprising a plastic container with a first chamber and a second chamber, where the chambers are separated from one another by a soluble and/or breakable dividing system, and the first chamber holds the first component and the second chamber holds the second component. Releasing and/or breaking of the dividing system leads to mixing of the two components and results in the ready-to-use dialysis solution. The first chamber and the second chamber are preferably arranged adjacent to one another in the container and are separated from one another by the dividing system. The dividing system is preferably a dividing seam (e.g., a soluble or breakable weld). The dividing seam is preferably opened by applying a pressure to one of the chambers whereupon the dividing seam breaks or dissolves and the contents of the two chambers become mixed and the mixture may be used as a ready-to-use dialysis solution in the dialysis treatment.

The first component of the inventive kit is preferably a sterile solution containing an acid and having a pH of ≤6.0; the second component is preferably also a sterile solution, preferably containing a buffer and having a pH≥7.0.

The inventive steviol glycoside derivatives may be contained in the first component or in the second component as well as in both components in the same or different concentrations. In one preferred embodiment, the inventive steviol glycoside is contained only in the first (acidic) component. In another preferred embodiment, the inventive steviol glycoside derivative is contained only in the second (basic) component. The first component and/or the second component and/or the optional additional component(s) may contain one or more electrolytes or also buffers.

In yet another preferred embodiment, the multichamber container is preferably a three-chamber bag comprising a plastic container with a first chamber, a second chamber, and a third chamber wherein the chambers are separated from one another by a soluble and/or breakable dividing system. The first chamber holds the first component, the second chamber holds the second component, and the third chamber holds the third component. Releasing and/or breaking of the dividing system leads to mixing of the three components and results in the ready-to-use dialysis solution. The chambers are preferably arranged adjacent to one another in the container and are separated from one another by the dividing system. The dividing system is preferably a dividing seam (e.g., a soluble or breakable weld). The dividing seam is preferably opened by applying a pressure to one of the chambers whereupon the dividing seam breaks or dissolves and the contents of the three chambers become mixed and the mixture may be used as a ready-to-use dialysis solution in the dialysis treatment.

The first component of the inventive kit is preferably a sterile solution containing an acid and having a pH of ≤6.5. The second component is preferably a sterile solution, preferably containing a buffer and having a pH≥7.5. The third component is preferably also a sterile solution, preferably containing a buffer and having a neutral pH of about 7.0.

The inventive steviol glycoside derivatives may be contained in the first (acidic) component or in the second (basic) component or in the third (neutral) component or in all three components in the same or different concentrations. In one preferred embodiment, the inventive steviol glycoside is contained only in the third (neutral) component.

Those skilled in the art will recognize that mixing the individual components usually involves a dilution effect for the case when the components contain the ingredients in different concentrations. For example, if the inventive steviol glycoside derivatives are contained exclusively in one of the components, mixing these components with at least one other component will lead to an increase in the volume with respect to the amount of the inventive steviol glycoside derivatives present and thus will result in a dilution effect, i.e., a decline in the concentration of steviol glycoside derivatives; consequently the components will preferably contain the inventive steviol glycoside derivatives in a higher concentration than the ready-to-use dialysis solution.

The concentration of inventive steviol glycoside or inventive steviol glycoside derivatives in the component is preferably close to the saturation concentration at a temperature of 5° C. in order to ensure adequate stability in storage at higher temperatures.

In a preferred embodiment, the total weight concentration of inventive steviol glycoside or starch derivatives in the component is 0.01 g/L to 1.0 kg/L, more preferably 0.1 to 750 g/L, even more preferably 1.0 to 500 g/L, most preferably 10 to 250 g/L and in particular 15 to 200 g/L. In another preferred embodiment, the total weight concentration of inventive steviol glycoside or steviol glycoside derivatives in the component is 25±24 g/L, g/L, more preferably 25±20 g/L, even more preferably 25±15 g/L, most preferably 25±10 g/L and in particular 25±5 g/L. In another preferred embodiment, the total weight concentration of inventive steviol glycoside or starch derivatives in the component is 50±25 g/L, more preferably 50±20 g/L, even more preferably 50±15 g/L, most preferably 50±10 g/L and in particular 50±5 g/L. In another preferred embodiment, the total weight concentration of inventive steviol glycoside or starch derivatives in the component is 75±25 g/L, more preferably 75±20 g/L, even more preferably 75±15 g/L, most preferably 75±10 g/L and in particular 75±5 g/L. In another preferred embodiment, the total weight concentration of inventive steviol glycoside or starch derivatives in the component is 100±25 g/L, more preferably 100±20 g/L, even more preferably 100±15 g/L, most preferably 100±10 g/L and in particular 100±5 g/L. In another preferred embodiment, the total weight concentration of inventive steviol glycoside or starch derivatives in the component is 200±25 g/L, more preferably 200±20 g/L, even more preferably 200±15 g/L, most preferably 200±10 g/L and in particular 200±5 g/L.

In a preferred embodiment, the second component contains the total amount of inventive steviol glycoside and a suitable buffer which adjusts the pH of the second component to more than 7.0, more preferably to more than 7.5, even more preferably to more than 8.0, most preferably more than 8.5 and in particular more than 9.0. This may preferably be achieved by bicarbonate which may be present, for example, in the form of dissociated sodium bicarbonate and/or potassium bicarbonate. In another preferred embodiment, the second component is solid and comprises a powdered mixture containing at least one inventive steviol glycoside or at least one inventive steviol glycoside derivative and at least one buffer, e.g., sodium and/or potassium bicarbonate.

The multichamber bag is preferably suitable for producing a dialysis solution which can be used in the peritoneal dialysis treatment and preferably contains the following ingredients in the following concentrations as the final concentration:

$Ca^{2+}$ 0.5 to 5 mEq/L;
$Mg^{2+}$ 0 to 3.0 mEq/L;
$Cl^-$ 90.5 to 121 mEq/L;
$K^+$ 0 to 4.0 mEq/L;
$HCO_3^-$ 25 to 40 mEq/L; wherein a chamber of the multichamber bag system contains a first acid concentrate and another chamber contains a second basic concentrate such that the acid concentrate contains $Ca^{2+}$ ions and the basic concentrate contains $HCO_3^-$ ions but no $Ca^{2+}$ ions; and the two concentrates can be mixed with one another after dissolving and/or breaking the dividing system (e.g., dividing seam) such that the mixing of the two concentrates leads to the preparation of the ready-to-use dialysis solution and the pH of the ready-to-use dialysis solution is 7.0 to 7.6.

The basic concentrate preferably contains a quantity of bicarbonate which leads to a bicarbonate concentration of the ready-to-use dialysis solution of at least 20 mM. The bicarbonate concentration of the basic component is preferably so high that the ready-to-use dialysis solution has a bicarbonate concentration of at least 25 mM.

The pH of the basic buffered second concentrate is preferably adjusted with hydrochloric acid.

The two concentrates are preferably mixed together in a volume ratio of 10:1 to 1:10 or 8:1 to 1:8, more preferably 5:1 to 1:5 or 3:1 to 1:3, even more preferably 2:1 to 1:2 and in particular 1:1.

The multichamber bag preferably has a gas barrier film which prevents gaseous $CO_2$ from escaping from the system. Those skilled in the art are familiar with gas barrier films.

A preferred subject matter of this invention relates to a method for preparing a dialysis solution in which the desired mixing ratio is automatically achieved by a dialysis machine or a peritoneal dialysis cycler.

In a preferred embodiment, the invention relates to a solid composition which is suitable for preparing the inventive dialysis solution by dissolving in a defined volume of a solvent (e.g., water). The solid composition is preferably a component as described above and is thus a component of the inventive kit. The solid composition contains the inventive steviol glycoside or steviol glycoside derivatives in any solid form, e.g., as a powder, granules, pellets, etc. The inventive steviol glycoside derivatives or the steviol glycoside may be present in spray-dried form or as a lyophilizate.

The inventive solid composition preferably contains a bicarbonate salt such as, for example, sodium or potassium bicarbonate. The substance quantity ratio of bicarbonate to inventive steviol glycoside or the steviol glycoside derivatives in the solid composition is preferably 1:100 to 100:1, more preferably 1:50 to 50:1, even more preferably 1:25 to 25:1, most preferably 1:10 to 10:1 and in particular 1:5 to 5:1.

The defined volume of solvent needed for preparing the inventive dialysis solution by dissolving the solid composition is preferably 1.0 to 2000 L. The solvent is preferably purified water, sterilized water or water for injection purposes which optionally contains one or more of the electrolytes described above, one or more osmotically active substance (e.g., at least one inventive steviol glycoside or steviol glycoside derivative) and/or one or more of the buffers described above.

Another subject matter of this invention relates to the use of at least one inventive steviol glycoside or at least one inventive steviol glycoside derivative for preparing the inventive dialysis solution (hemodialysis solution or peritoneal dialysis solution).

Another subject matter of this invention relates to the use of an inventive kit for preparing the inventive dialysis solution (hemodialysis solution or peritoneal dialysis solution).

Another subject matter of this invention relates to the use of an inventive solid composition for preparing the inventive dialysis solution (hemodialysis solution or peritoneal dialysis solution).

EXAMPLES

Example 1

For examples 2 to 7 standard CAPD solutions with a calcium content of 1.75 mmol/L were prepared. In one liter of water were dissolved 0.1017 g magnesium chloride hexahydrate (MgCl*6H$_2$O, 0.5 mmol/L), 0.2573 g calcium chloride dihydrate (CaCl$_2$*2 H$_2$O, 1.75 mmol/L), 5.786 g sodium chloride (NaCl, 99 mmol/L), and 7.847 g sodium lactate (50 wt. % solution, 35 mmol/L). To this solution were added either glucose (resulting in solutions with 2.27 wt. % and 4.25 wt. % glucose) or steviol glycosides (resulting in solutions with 3 wt. %, 6 wt. % and 9 wt. % steviol glycosides). The composition of the glucose-based solution is identical to one of the commercially available PD fluids stay-Safe® (Fresenius Medical Care).

Example 2

In this example the epithelial-to-mesenchymal transition (EMT) of human peritoneal mesothelial cells (HPMC) induced by TGF-β was investigated.

HPMC were isolated from omentum pieces precedent from elective surgeries. These cells were cultured on a collagen coated plate to reach sub-confluence and were then stimulated with TGF-β (1 ug/mL) in presence of the glucose or *stevia* fluids from example 1 (dilution at 50% with M199 medium) for 72 h and 7 days. FIG. 1 shows microscopic photographs of mesothelial cells in contact with PD solutions based on glucose (2.27 wt. % and 4.25 wt. %) and steviol glycosides (3 wt. %, 6 wt. % and 9 wt. %) at 72 h and at 7 days. PD solutions based on glucose induced cell disruption and inhibition of proliferation of mesothelial cells (MC) partial at 72 h and whole at 7 days. No cell disruption and inhibition of proliferation was observed with steviol glycosides PD solutions.

*Stevia* group samples showed a protective effect for epithelial-to-mesenchymal transition (EMT) induced by TGF-β. On the contrary, in the glucose group the EMT was favored.

Example 3

The effect of steviol glycoside containing PD fluids on EMT of human peritoneal mesothelial cells (HPMC) in vitro was compared to control.

HPMC were cultured and under sub-confluence conditions and were stimulated with TGF-β (positive control) and *Stevia* (3 wt. % and 6 wt. %) and *Stevia*+TGF-β (1 ng/mL). The negative control group was cultured with M199 medium. Gene expression of different EMT markers were analysed.

FIG. 2 summarizes the results of this experiment. The steviol glycoside containing PD solution modified the typical gene expression pattern associated with EMT. Snail expression after 24 h exposure was not increased in spite of TGF-β stimulus. Also, the e-cadherin expression at 24 h was not increased after TGF-β administration in contrast to control.

Example 4

Human peritoneal mesothelial cells (HPMC) at sub-confluence were cultured in the presence of *Stevia* (3 wt. % and 6 wt. %) and stimulated with or without TGF-β (1 ng/mL). The negative control group did not receive any stimulus. Collagen-I and fibronectin were determined at 72 h and 7 days (qPCR).

FIG. 3 shows the effect of steviol glycoside PD fluids on EMT of mesothelial cells in vitro. Collagen-I and fibronectin did not increase in spite of TGF-β stimulus.

Example 5

Human peritoneal mesothelial cells (HPMC) at sub-confluence were cultured in presence of the glucose- and *stevia*-based PD fluids from example 1 (dilution at 50% with M199 medium) and stimulated with or without TGF-β (1 ng/mL). The negative control group did not receive any stimulus. The capability of MCs to produce VEGF was measured at 72 h and 7 days.

FIG. 4 compares the effect of steviol glycoside and glucose-based PD fluids on the production of VEGF by mesothelial cells in vitro after TGF-β stimulus. Steviosides do not stimulate the VEGF production in comparison to glucose and TGF-β

Example 6

In this example the effect of stevioside-based and glucose-based PD fluids on the production of TGF-β by mesothelial cells was investigated.

Human peritoneal mesothelial cells (HPMC) at sub-confluence were cultured in presence of *stevia* (3 wt. % and 6 wt. %) and glucose (2.27 wt. % and 4.25 wt. %) based PD fluids from example 1 (dilution at 50% with M199 medium). The negative control group did not receive any stimulus. The capability to produce TGF-β by the MCs was measured at 72 h and 7 days. The results are summarized in FIG. 5. Steviol glycoside based PD fluids did not induce TGF-β production.

Example 7

The water and solute peritoneal transport of glucose-based (4.25 wt. % glucose) and *stevia*-based (1.5 wt. % steviosides) PD fluids was compared in a mouse and a rat model. The rats and mice received an injection (rats 10 mL and mice 1.5 mL) of either glucose-based or *stevia*-based PD fluid into the abdominal cavity using a syringe with a hypodermic needle. After dwell times of 30, 60, 90, 120, or 240 min five mice or rats each were sacrificed and the peritoneal fluid was collected for further analysis.

Peritoneal fluid and cells were separated by centrifugation. Cell populations were analyzed by flow cytometry. Pro-inflammatory cytokines (IL-6, TNF-α), TGF, VEGF, IL-6 and IL-10 and adipocytokines (leptin and adiponectin were determined in the liquid.

The osmolality of the PD fluids was determined with an osmometer based on the method of freezing-point depression. (Cryoscopic Osmometer, Osmomat 30, Gonotec Gesellschaft für Meβ-und Regeltechnik mbH, 2005).

FIG. 6 compares the intraperitoneal osmolality of glucose-based (4.25 wt. % glucose) and *stevia*-based (1.5 wt. %) PD fluids at various dwell times in rats. The *stevia*-based PD fluid maintained its osmolality while the glucose-based fluid lost it.

FIG. 7 compares the ultrafiltration rate of glucose-based (4.25 wt. % glucose) and *stevia*-based (1.5 wt. %) PD fluids at various dwell times in rat s. The *stevia*-based PD fluid maintained its ultrafiltration capacity independent of its osmolality while the glucose-based fluid lost ultrafiltration capacity after 120 min dwell time.

FIG. 8 compares the ultrafiltration rate of glucose-based (4.25 wt. % glucose) and *stevia*-based (1.5 wt. %) PD fluids at various dwell times in mice. The *stevia*-based PD fluid gained ultrafiltration capacity with dwell time while the glucose-based fluid lost ultrafiltration capacity over dwell time.

FIG. 9 compares the sodium concentration of glucose-based (4.25 wt. % glucose) and *stevia*-based (1.5 wt. %) PD fluids at various dwell times in rats. The *stevia*-based PD fluid showed low sodium sieving while a strong sodium sieving occurred for the glucose-based fluid.

According to these results, the *stevia* based PD fluids exhibit similar properties as icodextrin based PD fluids (as reported by Rippe and Levin in Kidney International, Vol. 57 (2000), 2546-2556).

Example 8

The solution of example 1 was used to prepare single chamber bags. In 950 mL of water 0.1017 g magnesium chloride hexahydrate (MgCl*6H$_2$O, 0.5 mmol/L), 0.2573 g calcium chloride dihydrate (CaCl$_2$*2 H$_2$O, 1.75 mmol/L), 5.786 g sodium chloride (NaCl, 99 mmol/L), and 7.847 g sodium lactate (50 wt. % solution, 35 mmol/L) were dissolved. To this solution 30.0 g steviol glycosides were added resulting in a solutions with 3 wt. % steviosides. The pH of the solution was adjusted to pH=6.0 by addition of 1.2 mL of 1 mmol/L NaOH solution. Finally, the solution was topped off to 1000 mL and filtered through membrane prefilters and then through membrane sterile filters into a single-chamber multilayer film bag and sealed with connectors. The dry bag was then repackaged into a bag and next heat sterilized at 121° C.

Example 9

This example describes the preparation of double chamber bags. To prepare 3 L of the acidic solution A, 33.84 g sodium chloride, 1.544 g calcium chloride×2H$_2$O, 0.610 g magnesium chloride×6H$_2$O, and 559.8 g steviol glycoside were dissolved in water and topped off to 3000 mL. To prepare the second individual solution B, 4.27 g sodium chloride and 5.38 g sodium bicarbonate were dissolved in water and topped off to 1000 mL. A necessary correction in the pH of the second solution to 8.2 was performed by adding 0.12 g sodium hydroxide. The two solutions were filtered through membrane prefilters and then through membrane sterile filters into a cooling tank. After checking the batch and releasing the solutions, they were filled into a multichamber multilayer film bag and sealed with connectors. The dry bag was then repackaged into a bag and next heat sterilized at 121° C.

Example 10

This example describes the preparation of triple chamber bags. To prepare 2 L of the acidic solution A, 33.84 g sodium chloride, 1.544 g calcium chloride×2H$_2$O, 0.610 g magnesium chloride×6H$_2$O, and were dissolved in water and topped off to 2000 mL. A necessary correction in the pH of the first solution to 8.2 was performed by adding 0.12 g sodium hydroxide.

To prepare the second basic solution B, 4.27 g sodium chloride and 5.38 g sodium bicarbonate were dissolved in water and topped off to 1000 mL. A necessary correction in the pH of the second solution to 8.2 was performed by adding 0.12 g sodium hydroxide.

To prepare the third individual solution C, 559.8 g steviol glycoside were dissolved in water and topped off to 1000 mL.

The three solutions were filtered through membrane prefilters and then through membrane sterile filters into a cooling tank. After checking the batch and releasing the solutions, they were filled into a multichamber multilayer film bag and sealed with connectors. The dry bag was then repackaged into a bag and next heat sterilized at 121° C.

The invention claimed is:

1. A steviol glycoside-derivative of the general structure I

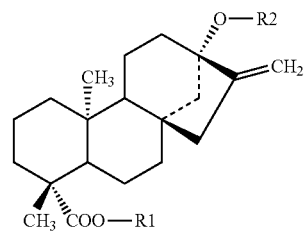

I wherein one of R1 and R2 is a polyethylene glycol unit polyethylene glycol unit —(CH$_2$—CH$_2$—O)$_n$—CH$_2$—CH$_2$—OH with n being an integer from 0 to 500, and one of R1 and R2 is H, a linear or branched C$_1$ to C$_6$ alkyl group, a polyethylene glycol unit —(CH$_2$—CH$_2$—O—)$_n$—CH$_2$—

CH$_2$—OH with n being an integer from 0 to 500, or one or more glucose, xylose or rhamnose units.

2. The steviol glycoside derivative according to claim 1, wherein the steviol is selected from the group consisting of Steviolbiosid, Steviosid, Rebaudiosid A, Rebaudiosid B, Rebaudiosid C, Rebaudiosid D, Rebaudiosid E, Rebaudiosid F and Dulkosid A.

3. The steviol glycoside derivative according to claim 1, wherein n is an integer from 0 to 100.

4. The steviol glycoside derivative according to claim 3, wherein n=0.

5. The steviol glycoside derivative according to claim 1, wherein one of R1 and R2 is a methyl, ethyl, n-propyl, iso-propyl, n-butyl, iso-butyl, tert-butyl, n-pentyl, or n-hexyl group.

6. The steviol glycoside derivative according to claim 1, wherein R1 is a methyl, ethyl, n-propyl, iso-propyl, n-butyl, iso-butyl, tert-butyl, n-pentyl, or n-hexyl group.

7. A dialysis solution containing at least one steviol glycoside derivative of the general structure according to claim 1.

8. A kit configured for preparing the dialysis solution according to claim 7, comprising a first component, a second component, and optionally one or more additional components, wherein said dialysis solution is obtained by mixing the first component with the second component and optionally with the additional component(s), and wherein the first or second component comprises the steviol glycoside derivative.

9. A kit according to claim 8, comprising a first component, a second component, and a third component, wherein said dialysis solution is obtained by mixing the first component with the second and the third component, and wherein the first or second component comprises the steviol glycoside derivative.

10. A kit according to claim 9 comprising
the first component with a pH≤6.5,
the second component with a pH≥7.5 and
the third component with a pH of about 7.

11. A solid composition configured for preparing the dialysis solution according to claim 7, wherein the dialysis solution is obtained by dissolving the solid composition in a solvent, and wherein the solid composition comprises the steviol glycoside derivative.

12. In a method of treating a patient for renal failure comprising dialysis of the patient's blood using a dialysis solution, the improvement comprising using the dialysis solution of claim 7.

13. The steviol glycoside according to claim 1 wherein R1 and R2 are independently a polyethylene glycol unit —(CH2-CH2-O-)n-CH2-CH2-OH with n being an integer from 0 to 500.

* * * * *